(12) United States Patent
Kartush

(10) Patent No.: US 10,687,937 B2
(45) Date of Patent: Jun. 23, 2020

(54) SYSTEMS AND METHODS FOR PERFORMING OSSICULAR CHAIN RECONSTRUCTIONS

(71) Applicant: Jack M. Kartush, Bloomfield Hills, MI (US)

(72) Inventor: Jack M. Kartush, Bloomfield Hills, MI (US)

(*) Notice: Subject to any disclaimer, the term of this patent is extended or adjusted under 35 U.S.C. 154(b) by 389 days.

(21) Appl. No.: 15/707,268

(22) Filed: Sep. 18, 2017

(65) Prior Publication Data

US 2018/0125641 A1   May 10, 2018

Related U.S. Application Data

(60) Provisional application No. 62/419,107, filed on Nov. 8, 2016.

(51) Int. Cl.
*A61F 2/18* (2006.01)
*A61F 11/00* (2006.01)

(52) U.S. Cl.
CPC ............ *A61F 2/18* (2013.01); *A61F 11/004* (2013.01); *A61F 2002/183* (2013.01); *A61F 2250/0006* (2013.01); *A61F 2250/0007* (2013.01)

(58) Field of Classification Search
CPC .. A61F 2/58; A61F 2/18; A61F 11/004; A61F 2002/183; A61F 2250/006; A61F 2250/007; A61H 1/0292
USPC ................................................. 601/5; 623/10
See application file for complete search history.

(56) References Cited

U.S. PATENT DOCUMENTS

| | | | |
|---|---|---|---|
| 4,281,419 A | 8/1981 | Treace | |
| 4,292,693 A | 10/1981 | Shea et al. | |
| 4,510,627 A | 4/1985 | Treace et al. | |
| 4,597,764 A | 7/1986 | Black | |
| 4,601,723 A | 7/1986 | McGrew | |
| 4,617,024 A | 10/1986 | Broemer et al. | |
| D286,909 S | 11/1986 | Black | |
| D286,910 S | 11/1986 | Black | |
| 4,624,672 A | 11/1986 | Lenkauskas | |
| 4,740,209 A | 4/1988 | Gersdorff | |
| 4,871,364 A | 10/1989 | Bays et al. | |
| 5,061,280 A | 10/1991 | Prescott | |
| 5,104,401 A | 4/1992 | Kurz | |

(Continued)

FOREIGN PATENT DOCUMENTS

| | | |
|---|---|---|
| CN | 101461743 B | 5/2012 |
| DE | 102005010705 B3 | 8/2006 |

(Continued)

OTHER PUBLICATIONS

International Search Report and Written Opinion of the International Searching Authority for PCT Application No. PCT/US2017/052161, dated Jan. 8, 2018.

(Continued)

*Primary Examiner* — Suba Ganesan
*Assistant Examiner* — Aren Patel
(74) *Attorney, Agent, or Firm* — Carlson, Gaskey & Olds

(57) ABSTRACT

This disclosure relates to systems and methods for performing ossicular reconstructions. An exemplary ossicular reconstruction system may include one or more adjustable prosthetic devices and micro-measuring devices. The adjustable prosthetic devices may be adjusted in terms of length, angulation, or both.

22 Claims, 15 Drawing Sheets

(56) References Cited

U.S. PATENT DOCUMENTS

| | | |
|---|---|---|
| 5,180,391 A | 1/1993 | Beoni |
| 5,554,188 A | 9/1996 | Prescott |
| 5,578,086 A | 11/1996 | Prescott |
| 6,387,128 B1 | 5/2002 | Kurz et al. |
| 6,432,139 B1 | 8/2002 | Elies et al. |
| 6,579,317 B2 | 6/2003 | Kurz |
| 6,726,719 B2 | 4/2004 | Antonelli et al. |
| 6,892,466 B2 | 5/2005 | Kurz et al. |
| 6,942,696 B1 | 9/2005 | White et al. |
| 7,011,683 B2 | 3/2006 | Antonelli et al. |
| 7,025,785 B1 | 4/2006 | Boyev |
| 7,087,081 B2 | 8/2006 | Prescott et al. |
| 7,553,328 B2 | 6/2009 | Steinhardt et al. |
| 7,628,812 B2 | 12/2009 | Awengen et al. |
| 7,658,764 B2 | 2/2010 | Reitan et al. |
| 7,955,386 B2 | 6/2011 | Reitan et al. |
| 8,057,542 B2 | 11/2011 | Kraus |
| 8,100,966 B2 | 1/2012 | Steinhardt et al. |
| 8,192,489 B2 | 6/2012 | Edwards |
| 8,206,444 B2 | 6/2012 | Reitan et al. |
| 8,262,729 B2 | 9/2012 | Bhansali |
| 8,435,291 B2 | 5/2013 | Wiens et al. |
| 8,506,628 B2 | 8/2013 | Kraus |
| 8,641,760 B2 | 2/2014 | Mendius et al. |
| 8,865,788 B2 | 10/2014 | Merrill et al. |
| 8,936,637 B2 | 1/2015 | Steinhardt et al. |
| 9,216,081 B2 | 12/2015 | Steinhardt et al. |
| 9,326,849 B2 | 5/2016 | Scheurer |
| 2004/0162614 A1 | 8/2004 | Steinhardt et al. |
| 2004/0167624 A1 | 8/2004 | Kurz et al. |
| 2004/0181280 A1 | 9/2004 | Antonelli et al. |
| 2004/0181281 A1 | 9/2004 | Antonelli et al. |
| 2005/0065603 A1 | 3/2005 | Prescott et al. |
| 2006/0241755 A1 | 10/2006 | Prescott et al. |
| 2007/0021833 A1 | 1/2007 | aWengen et al. |
| 2007/0055372 A1 | 3/2007 | Prescott et al. |
| 2007/0083263 A1 | 4/2007 | Steinhardt et al. |
| 2007/0255405 A1 | 11/2007 | Reitan et al. |
| 2008/0058927 A1 | 3/2008 | Brosnahan |
| 2008/0195201 A1 | 8/2008 | Steinhardt et al. |
| 2009/0149697 A1 | 6/2009 | Steinhardt et al. |
| 2009/0164010 A1 | 6/2009 | Steinhardt et al. |
| 2009/0198334 A1 | 8/2009 | Kraus |
| 2009/0240330 A1 | 9/2009 | Steinhardt et al. |
| 2009/0240332 A1* | 9/2009 | Steinhardt ............... A61F 2/18 623/10 |
| 2010/0010629 A1 | 1/2010 | Bhansali |
| 2010/0262236 A1 | 10/2010 | Steinhardt et al. |
| 2011/0046731 A1 | 2/2011 | Wiens et al. |
| 2011/0054607 A1 | 3/2011 | Reitan et al. |
| 2012/0065730 A1* | 3/2012 | Edwards ............... A61B 17/29 623/10 |
| 2012/0330416 A1 | 12/2012 | Bhansali |
| 2014/0094910 A1* | 4/2014 | Steinhardt ............... A61F 2/18 623/10 |
| 2014/0364947 A1 | 12/2014 | Scheurer |
| 2017/0048628 A1* | 2/2017 | McElveen ............... A61F 2/18 |

FOREIGN PATENT DOCUMENTS

| | | |
|---|---|---|
| DE | 102005027215 A1 | 12/2006 |
| DE | 102005048618 A1 | 4/2007 |
| DE | 102005027215 B4 | 9/2007 |
| EP | 1438931 A1 | 7/2004 |
| EP | 1759662 A1 | 3/2007 |
| EP | 2030595 A2 | 3/2009 |
| EP | 2072026 A1 | 6/2009 |
| WO | WO2012033566 A1 | 3/2012 |
| WO | WO2012154404 A1 | 11/2012 |

OTHER PUBLICATIONS

Kartush, et al., "Contemporary ossiculoplastic options," Current Opinion in Otolaryngology & Head and Neck Surgery 2001, 9:272-278.

Kartush, et al., "Ossicular Chain Reconstruction: Maximizing Success and Minimizing Errors," Chapter 9, Ossicular Chain Reconstruction, pp. 90-101.

Kartush, "Ossicular Chain Reconstructions, Capitulum to Malleus," Otolaryngologic Clinics of North America, vol. 27, No. 4, Aug. 1994, pp. 689-715.

Kartush, et al., "Over-Under Tympanoplasty," The Largyngoscope 112: May 2002, pp. 802-807.

The International Preliminary Report on Patentability for PCT Application No. PCT/US2017/052161, dated May 23, 2019.

* cited by examiner

SYSTEMS AND METHODS FOR PERFORMING OSSICULAR CHAIN RECONSTRUCTIONS

CROSS-REFERENCE TO RELATED APPLICATIONS

This application claims priority to U.S. Provisional Application No. 62/419,107, which was filed on Nov. 8, 2016.

TECHNICAL FIELD

This disclosure relates to systems and methods for performing ossicular chain reconstructions. An exemplary ossicular reconstruction system may include a prosthetic device having an adjustable length and an adjustable angulation. The system may further include a micro-measuring device for accurately accessing the proper length and angulation of the prosthetic device for a given clinical need.

BACKGROUND

The human middle ear includes the tympanic membrane (i.e., the ear drum) and three ossicles. The three ossicles include the malleus (i.e., the hammer), the incus (i.e., the anvil) and the stapes (i.e., the stirrup). Sound vibrates the tympanic membrane which in turn vibrates the ossicles. The ossicles facilitate the conduction of sound waves from the tympanic membrane to the inner ear and are therefore important for hearing.

One or more of the ossicles may require surgical replacement due to disease, trauma, or congenital anomalies. Ossicular prostheses are commonly used for reconstructing an entirety of, or portions of, the ossicular chain to improve hearing. Determining the proper length and angulation of the prosthesis to be implanted may be difficult because of the relatively small operative field the surgeon must work in and because of differences in anatomy from patient-to-patient. Accordingly, additional advances in this surgical field are desired.

SUMMARY

This disclosure relates to systems and methods for performing ossicular reconstructions. An exemplary ossicular reconstruction system may include one or more adjustable prosthetic devices and micro-measuring devices.

A prosthetic device for performing ossicular reconstructions according to an exemplary aspect of the present disclosure includes, among other things, a body extending along a longitudinal axis and including a first fastener segment, a second fastener segment, and a central segment between the first fastening segment and the second fastening segment. The central segment is adjustable to either lengthen or shorten the body in a direction that is coaxial with the longitudinal axis.

In a further non-limiting embodiment of the foregoing prosthetic device, a portion of the central segment includes an adjustable angle to position the body non-linearly along the longitudinal axis.

In a further non-limiting embodiment of either of the foregoing prosthetic devices, the first fastener segment is configured for connecting the body to a tympanic membrane or a component of an ossicular chain, and the second fastener segment is configured for connecting the body to tissue near an inner ear or another component of the ossicular chain.

In a further non-limiting embodiment of any of the foregoing prosthetic devices, the first fastener segment is either a flat disk or a U-shaped cradle.

In a further non-limiting embodiment of any of the foregoing prosthetic devices, the second fastener segment is either a shoe or a cupped socket.

In a further non-limiting embodiment of any of the foregoing prosthetic devices, the central segment includes a plurality of arched plates that are arranged together to form a spherical shape.

In a further non-limiting embodiment of any of the foregoing prosthetic devices, each of the plurality of arched plates are compressible to shorten the body and straightenable to lengthen the body.

In a further non-limiting embodiment of any of the foregoing prosthetic devices, each of the plurality of arched plates includes at least one fenestration.

In a further non-limiting embodiment of any of the foregoing prosthetic devices, the central segment includes a plurality of jointed limbs.

In a further non-limiting embodiment of any of the foregoing prosthetic devices, each of the plurality of jointed limbs includes struts that are pivotally connected at a joint.

In a further non-limiting embodiment of any of the foregoing prosthetic devices, the central segment includes a telescoping tube assembly having a rod that is movable within a tube.

A method for performing an ossicular reconstruction according to another exemplary aspect of the present disclosure includes, among other things, using a measuring device to determine a size and an angulation of a prosthetic device that is necessary for reconstructing at least a portion of an ossicular chain of a middle ear, adjusting a length and an angulation of the prosthetic device to match the measurements obtained using the measuring device, and implanting the prosthetic device into the middle ear.

In a further non-limiting embodiment of the foregoing method, adjusting the length and the angulation of the prosthetic device occurs before implanting the prosthetic device into the middle ear.

In a further non-limiting embodiment of either of the foregoing methods, adjusting the length and the angulation of the prosthetic device occurs after implanting the prosthetic device into the middle ear.

In a further non-limiting embodiment of any of the foregoing methods, the method includes readjusting the length or the angulation of the prosthetic device after implanting the prosthetic device into the middle ear.

In a further non-limiting embodiment of any of the foregoing methods, using the measuring device includes inserting the measuring device into the middle ear, maneuvering a template of the measuring device to achieve a desired positioning of the template relative to the ossicular chain, and assessing the length and the angulation necessary for reconstructing the ossicular chain based on the positioning of the template.

In a further non-limiting embodiment of any of the foregoing methods, adjusting the length and the angulation of the prosthetic device includes manipulating an arched plate of the prosthetic device.

In a further non-limiting embodiment of any of the foregoing methods, adjusting the length and the angulation of the prosthetic device includes manipulating a jointed limb of the prosthetic device.

In a further non-limiting embodiment of any of the foregoing methods, adjusting the length and the angulation of the prosthetic device includes manipulating a telescoping tube assembly of the prosthetic device.

A system for performing ossicular reconstructions according to another exemplary aspect of the present disclosure includes, among other things, an adjustable prosthetic device and a measuring device including an elongated shaft and a template movably connected to the elongated shaft. The template includes a size and a shape corresponding to that of the adjustable prosthetic device for reconstructing at least a portion of an ossicular chain of an inner ear.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure describes systems and methods for performing ossicular reconstructions. An exemplary system may include one or more adjustable prosthetic devices and micro-measuring devices that allow for the length and the angulation of the prosthetic device to be adjusted by the surgeon within the operative field. These and other features of this disclosure are discussed in greater detail below.

Figure 1:
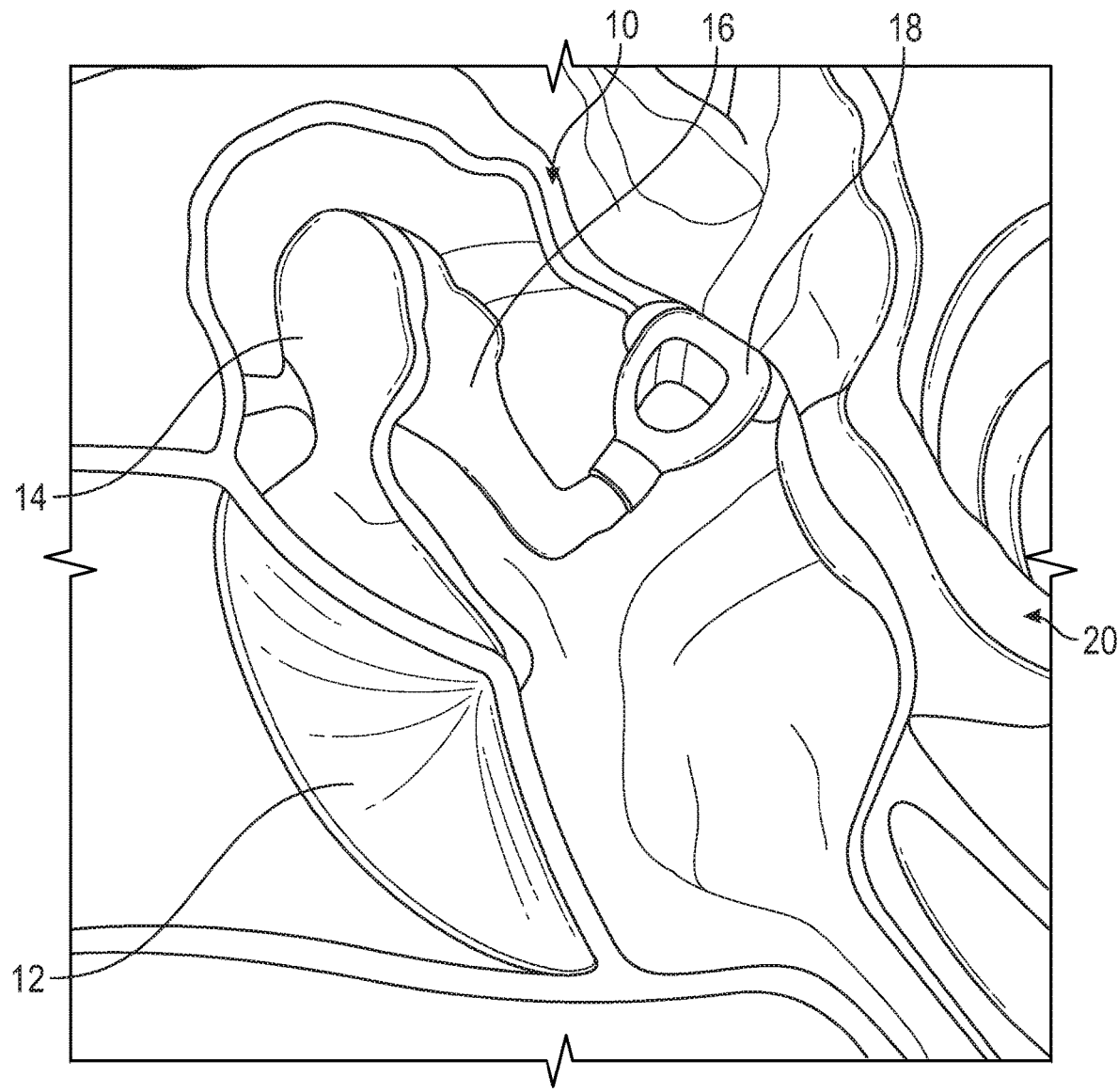
FIG. 1 is a cross-sectional view of a human middle ear.

FIG. 1 illustrates a human middle ear 10. The middle ear 10 includes a tympanic membrane 12, or eardrum, and three ossicles: the malleus 14, the incus 16, and the stapes 18. Collectively, the malleus 14, the incus 16, and the stapes 18 are referred to as the ossicular chain of the middle ear 10. The malleus 14, the incus 16, and the stapes 18 are arranged in order extending laterally to medially within the middle ear 10.

Sound waves vibrate the tympanic membrane 12, thus causing the malleus 14, the incus 16, and the stapes 18 to vibrate. The malleus 14, incus 16, and stapes 18 transmit the sound waves to a fluid filled inner ear 20. The transmission of the sound waves to the inner ear 20 by the ossicular chain is essential for hearing.

One or more portions of the ossicular chain may become missing or damaged due to disease, trauma, or congenital anomalies. As a result, the sound waves may be transmitted incompletely by the ossicular chain, thus resulting in hearing loss. This disclosure describes systems and methods for reconstructing an entirety of, or portions of, the ossicular chain in order to improve the transfer of sound waves between the tympanic membrane 12 and the inner ear 20. The systems and methods of this disclosure for performing ossicular reconstructions may include the use of various adjustable prosthetic devices and micro-measuring devices. Multiple embodiments of these types of devices are discussed in detail below.

Figure 2:
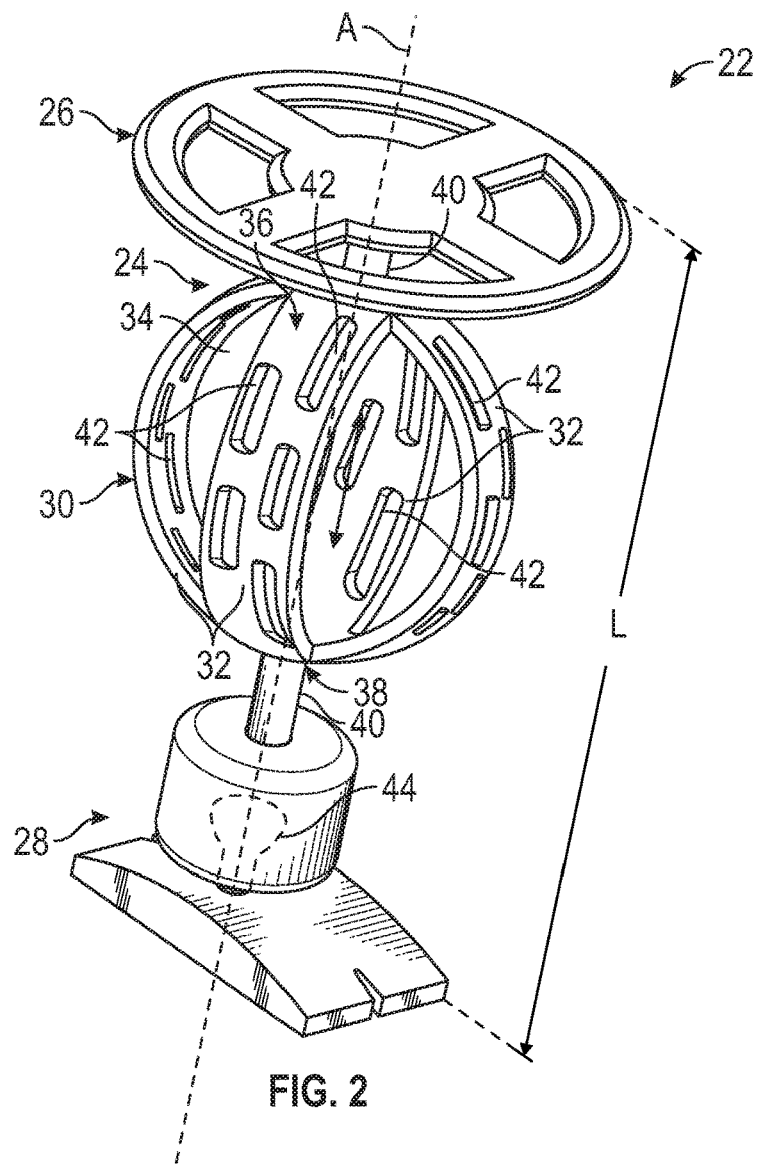
FIG. 2 illustrates a prosthetic device according to a first embodiment of this disclosure.

FIG. 2 illustrates an exemplary prosthetic device 22 for performing ossicular reconstructions. The prosthetic device 22 includes a body 24 disposed along a longitudinal axis A. The prosthetic device 22 may be made of metallic materials, plastic materials, ceramic materials, or any other suitable biocompatible materials. In a non-limiting embodiment, the prosthetic device 22 is made of titanium, platinum, hydroxylapetite, or any combination of two or more of these materials. However, it should be understood that the type of material used to construct the prosthetic device 22 is not intended to limit this disclosure.

The body 24 includes a first fastening segment 26, a second fastening segment 28, and a central segment 30 between the first fastening segment 26 and the second fastening segment 28. The first fastening segment 26 is configured for connecting the prosthetic device 22 to the tympanic membrane or a component of the ossicular chain, and the second fastening segment 28 is configured for connecting the prosthetic device 22 to another component of the ossicular chain, or to contact tissues adjacent to the inner ear. Once implanted, the first fastening segment 26 is positioned at a lateral side of the middle ear (i.e., toward the tympanic membrane) and the second fastening segment 28 is positioned at a medial side of the middle ear (i.e., toward the inner ear).

The central segment 30 is adjustable to alter a length L of the body 24 along the longitudinal axis A. The length L may be shortened or lengthened by adjusting the central segment 30 in a direction coaxial with the longitudinal axis A.

In a non-limiting embodiment, the central segment 30 includes a plurality of arched plates 32 that are arranged together to form a spherical shape. The arched plates 32 are arched in a radially outward direction relative to the longitudinal axis A to establish an open space 34 between the arched plates 32. The arched plates 32 may meet together at a top part 36 of the central segment 30, which faces the first fastening segment 26, and at a bottom part 38 of the central segment 30, which faces the second fastening segment 28. The central segment 30 may optionally include first and second shafts 40 that connect between the top part 36 and the first fastening segment 26 and between the bottom part 38 and the second fastening segment 28, respectively.

Figure 2A:
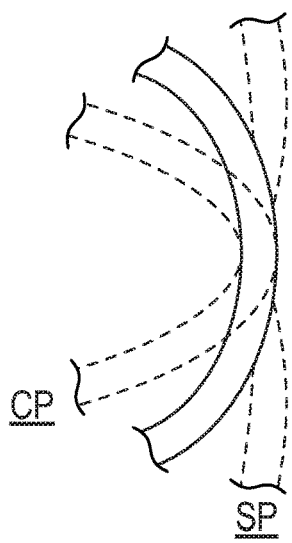
FIG. 2A illustrates different positions of an arched plate of the prosthetic device of FIG. 2.

The arched plates 32 may be compressed to decrease the length L, or may be expanded apart to increase the length L. For example, in a non-limiting embodiment, the length L can be decreased by moving the top part 36 and the bottom part 38 of the central segment 30 toward one another, thereby moving each arched plate 32 toward a more collapsed position CP (see FIG. 2A). In the collapsed position CP, the arched plates 32 are compressed and therefore approach a U-shape. In another non-limiting embodiment, the length L can be increased by moving the top part 36 and the bottom part 38 further apart from each other, thereby moving each arched plate 32 toward a more straightened position SP (see FIG. 2A). In the straightened position SP, the arched plates 32 are expanded and therefore approach are more linear shape. The length L of the prosthetic device 22 can adjusted either in situ or ex situ after determining the desired length of the prosthetic device 22.

The central segment 30 can also be modified to adjust an angulation of the prosthetic device 22. For example, in another non-limiting embodiment, one or more of the arched plates 32 can be bent to position the central segment 30 off-axis relative to the longitudinal axis A. In the off-axis position, the body 24 of the prosthetic device 22 is non-linear along the longitudinal axis A.

The adjustability (e.g., in terms of both length and angulation) of the central segment 30 can be controlled by a variety of factors. For example, the adjustability of the prosthetic device 22 can be controlled by altering the malleability of the central segment 30, by changing the number of arched plates 32 that make up the central segment 30, by changing a thickness of the arched plates 32, by changing a width of the arched plates 32, etc.

In another non-limiting embodiment, the adjustability of the central segment 30 is controlled by providing one or more fenestrations 42 through each arched plate 32. The fenestrations 42 are openings formed through the arched plates 32 which alter the malleability of the central segment 30. The malleability of the central segment 30 can be selected to allow in situ adjustments in size and angulation of the prosthetic device 22 while still providing sufficient rigidity to resist shape changes once a desired size and angulation has been determined and implemented.

The prosthetic device 22 of FIG. 2 is particularly suited for a total ossicular reconstruction that substantially reconstructs each of the malleus, the incus, and the stapes. In this non-limiting embodiment, the first fastening segment 26 includes a flat disk that contacts the tympanic membrane and the second fastening segment 28 includes a shoe that contacts the footplate of the stapes. In another non-limiting embodiment, the second fastening segment 28 includes a ball joint 44 that allows the shoe to swivel relative to the rest of the prosthetic device 22.

Figure 3:
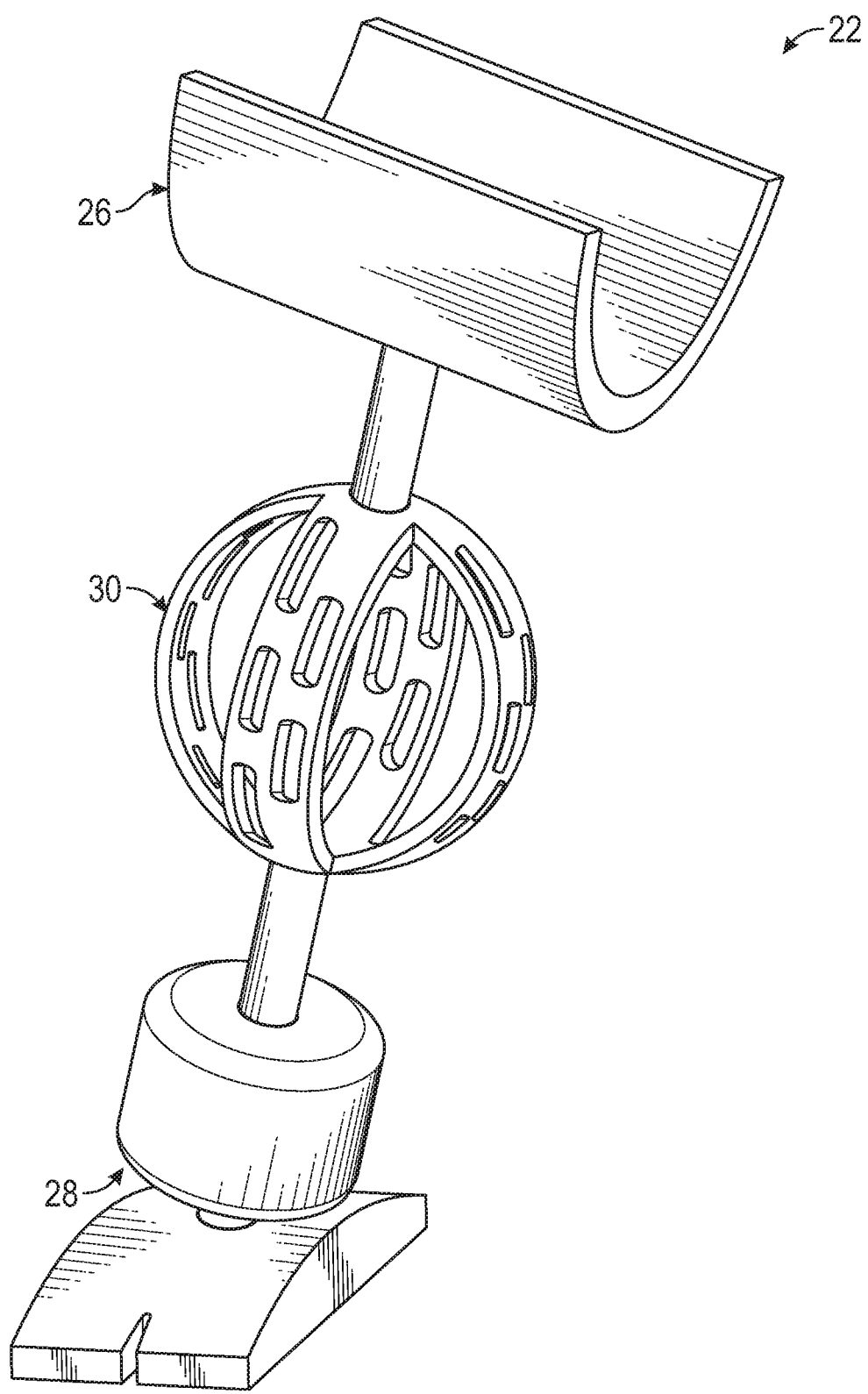
FIG. 3 illustrates another exemplary design configuration of the prosthetic device of FIG. 2.

The first fastening segment 26 and the second fastening segment 28 of the prosthetic device 22 may include various other designs depending on the clinical need. The clinical need may be based on the type and severity of the damage to the ossicular chain, among other factors. For example, in the non-limiting embodiment of FIG. 3, the first fastening segment 26 includes a U-shaped cradle that rests on the undersurface of the malleus and the second fastenings segment 28 includes a shoe that contacts the footplate of the stapes. The design of FIG. 3 is particularly suited for a total incus-stapes reconstruction.

Figure 4:
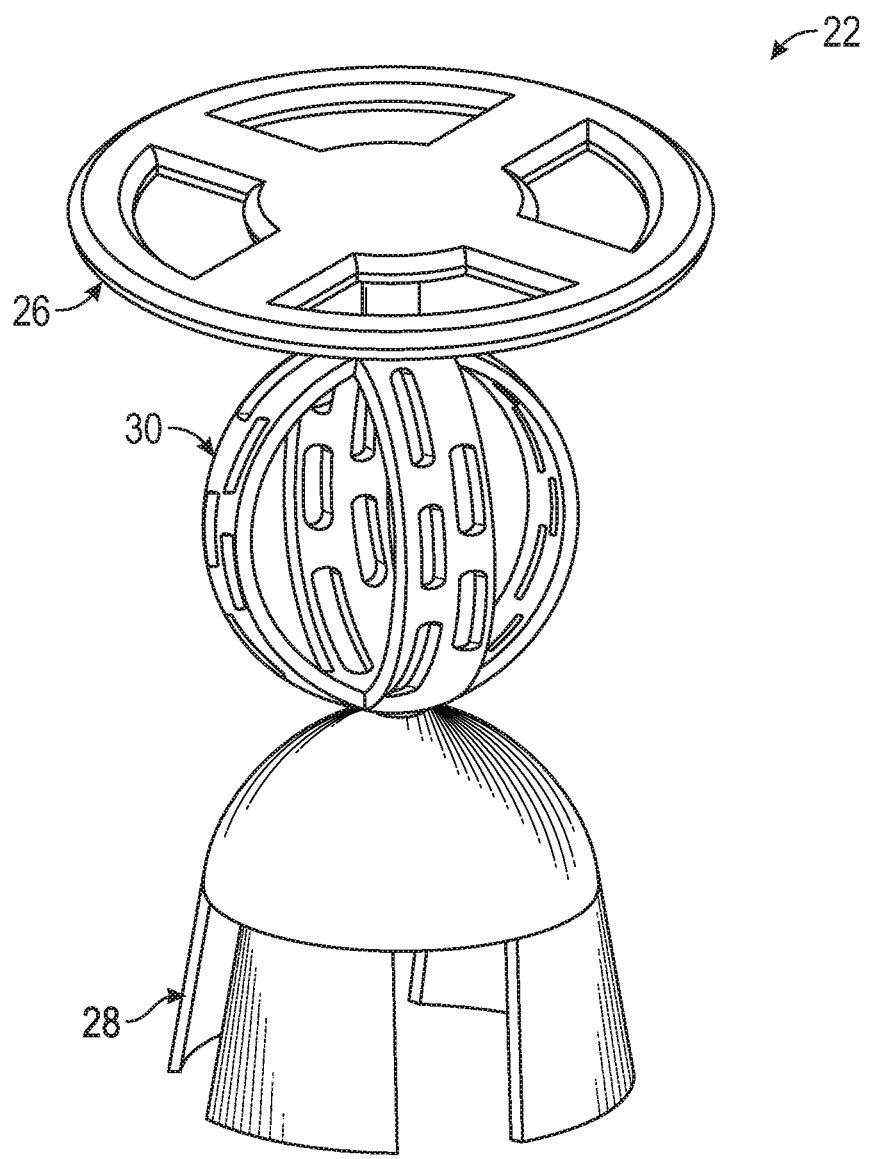
FIG. 4 illustrates another exemplary design configuration of the prosthetic device of FIG. 2.

The prosthetic device 22 may also be configured to achieve partial ossicular chain reconstructions. For example, as shown in the non-limiting embodiment of FIG. 4, the first fastening segment 26 includes a flat disk that contacts the tympanic membrane and the second fastening segment 28 includes a cupped socket that can be received on the capitulum of the stapes. The design of FIG. 4 is particularly suited for a partial ossicular reconstruction that reconstructs the incus.

Figure 5:
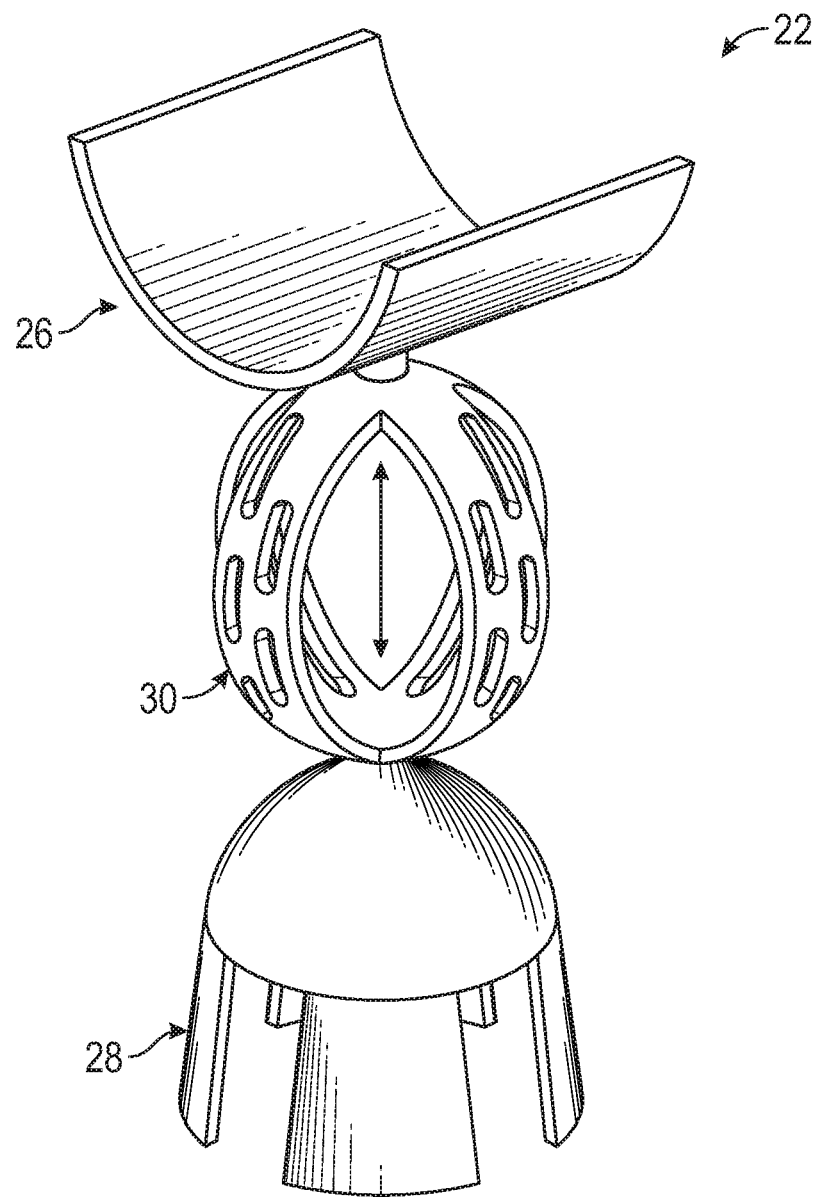
FIG. 5 illustrates yet another exemplary design configuration of the prosthetic device of FIG. 2.

In yet another non-limiting embodiment, shown in FIG. 5, the first fastening segment 26 includes a U-shaped cradle that rests on the undersurface of the malleus and the second fastenings segment 28 includes a cupped socket that can be received on the capitulum of the stapes. The design of FIG. 5 is particularly suited for a partial ossicular reconstruction that reconstructs the incus.

Figure 6:
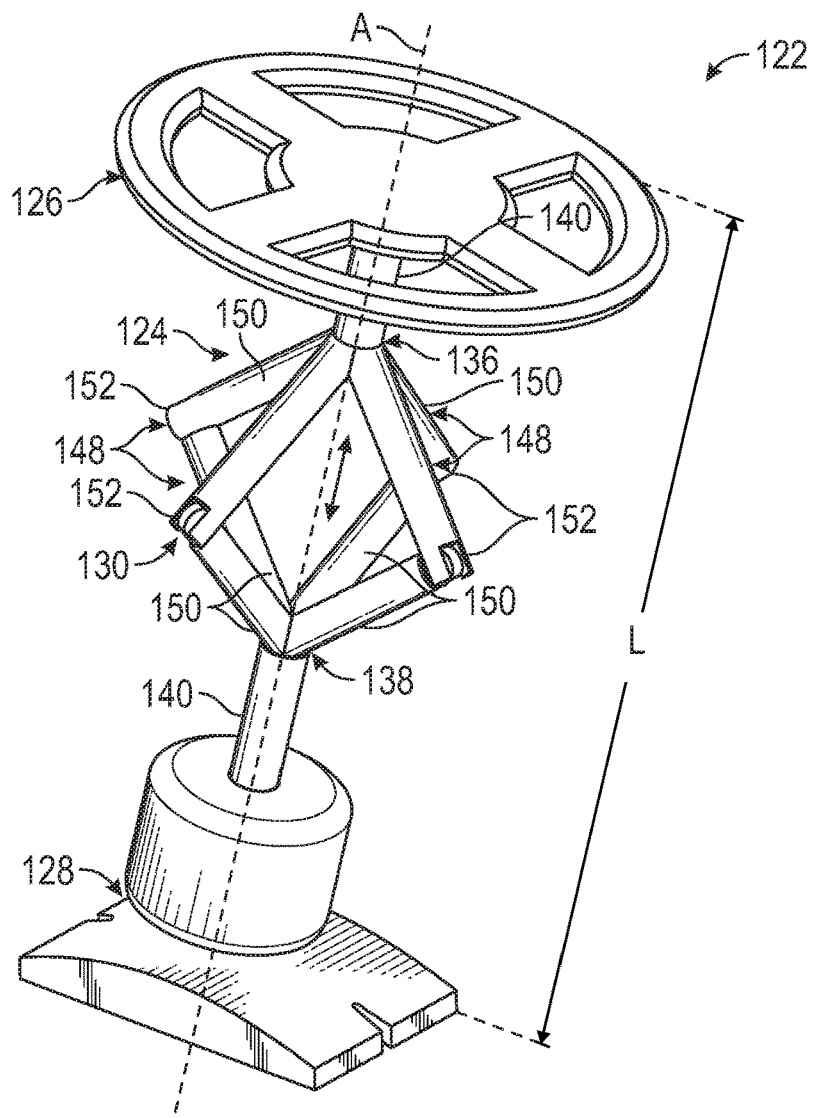
FIG. 6 illustrates a prosthetic device according to a second embodiment of this disclosure.
Figure 6A:
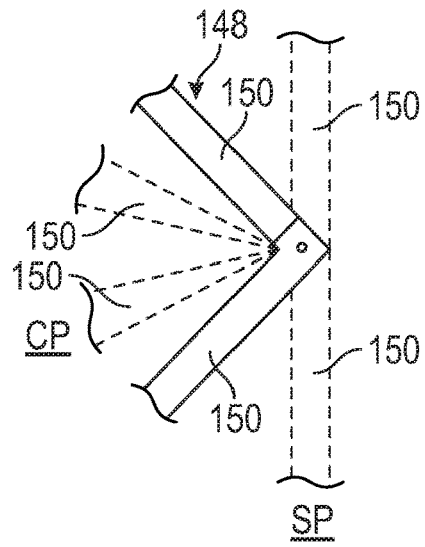
FIG. 6A illustrates different positions of a jointed limb of the prosthetic device of FIG. 2.

FIG. 6 illustrates another exemplary prosthetic device 122 for performing ossicular reconstructions. The prosthetic device 122 includes a body 124 disposed along a longitudinal axis A. The body 124 includes a first fastening segment 126, a second fastening segment 128, and a central segment 130 connected between the first fastening segment 126 and the second fastening segment 128. The first fastening segment 126 is configured for connecting the prosthetic device 122 to the tympanic membrane or a component of the ossicular chain, and the second fastening segment 128 is configured for connecting the prosthetic device 122 to another component of the ossicular chain, or to contact tissues adjacent to the inner ear.

The central segment 130 is adjustable to alter a length L of the body 124 along the longitudinal axis A. The length L may be shortened or lengthened by adjusting the central segment 130 in a direction coaxial with the longitudinal axis A.

In a non-limiting embodiment, the central segment 130 includes a plurality of jointed limbs 148. Each jointed limb 148 is V-shaped and extends off-axis relative to the longitudinal axis A. Each jointed limb 148 may include at least two struts 150 and at least one joint 152. The struts 150 are pivotable relative to one another via the joints 152. In a non-limiting embodiment, each strut 150 extends along an axis that is transverse to the longitudinal axis A. The struts 150 of each jointed limb 148 meet together at a top part 136 and bottom part 138 of the central segment 130. The central segment 130 may optionally include first and second shafts 140 that connect between the top part 136 and the first fastening segment 126 and between the bottom part 138 and the second fastening segment 128, respectively.

The jointed limbs 148 may be expanded or contracted to alter the length L of the prosthetic device 122. For example, in a non-limiting embodiment, the length L can be decreased or shortened by collapsing the top part 136 and the bottom part 138 of the central segment 130 toward one another, thereby moving each jointed limb 148 toward a more collapsed position CP. In the collapsed position CP, the struts 150 are closer to one another and may approach direct contact with one another. In another non-limiting embodiment, the length L can be increased or lengthened by expanding the top part 136 and the bottom part 138 apart from each other, thereby moving each jointed limb 148 toward a more straightened position SP. In the straightened position SP, the struts 150 are further apart from one another and approach a more linear shape. The adjustment of the length L can be made either in situ or ex situ after determining the desired length of the prosthetic device 122.

The central segment 130 can also be modified to adjust an angulation of the prosthetic device 122. For example, in another non-limiting embodiment, one or more of the struts 150 of the jointed limbs 148 can be pivoted about the joints 152 to position the central segment 130 off-axis relative to the longitudinal axis A. In the off-axis position, the body 124 of the prosthetic device 122 is non-linear along the longitudinal axis A. In yet another non-limiting embodiment, the angulation of the prosthetic device 122 can be adjusted by adding one or more joints at the top part 136 and/or the bottom part 138 of the central segment 130 (i.e., at a junction between the shafts 140 and the central segment 130).

The prosthetic device 122 of FIG. 6 is particularly suited for a total ossicular reconstruction that substantially reconstructs each of the malleus, the incus, and the stapes. In this non-limiting embodiment, the first fastening segment 126 includes a flat disk that contacts the tympanic membrane and the second fastening segment 128 includes a shoe that contacts the footplate of the stapes. In another non-limiting embodiment, the second fastening segment 128 includes a ball joint 144 that allows the shoe to swivel relative to the rest of the prosthetic device 122.

Figure 7:
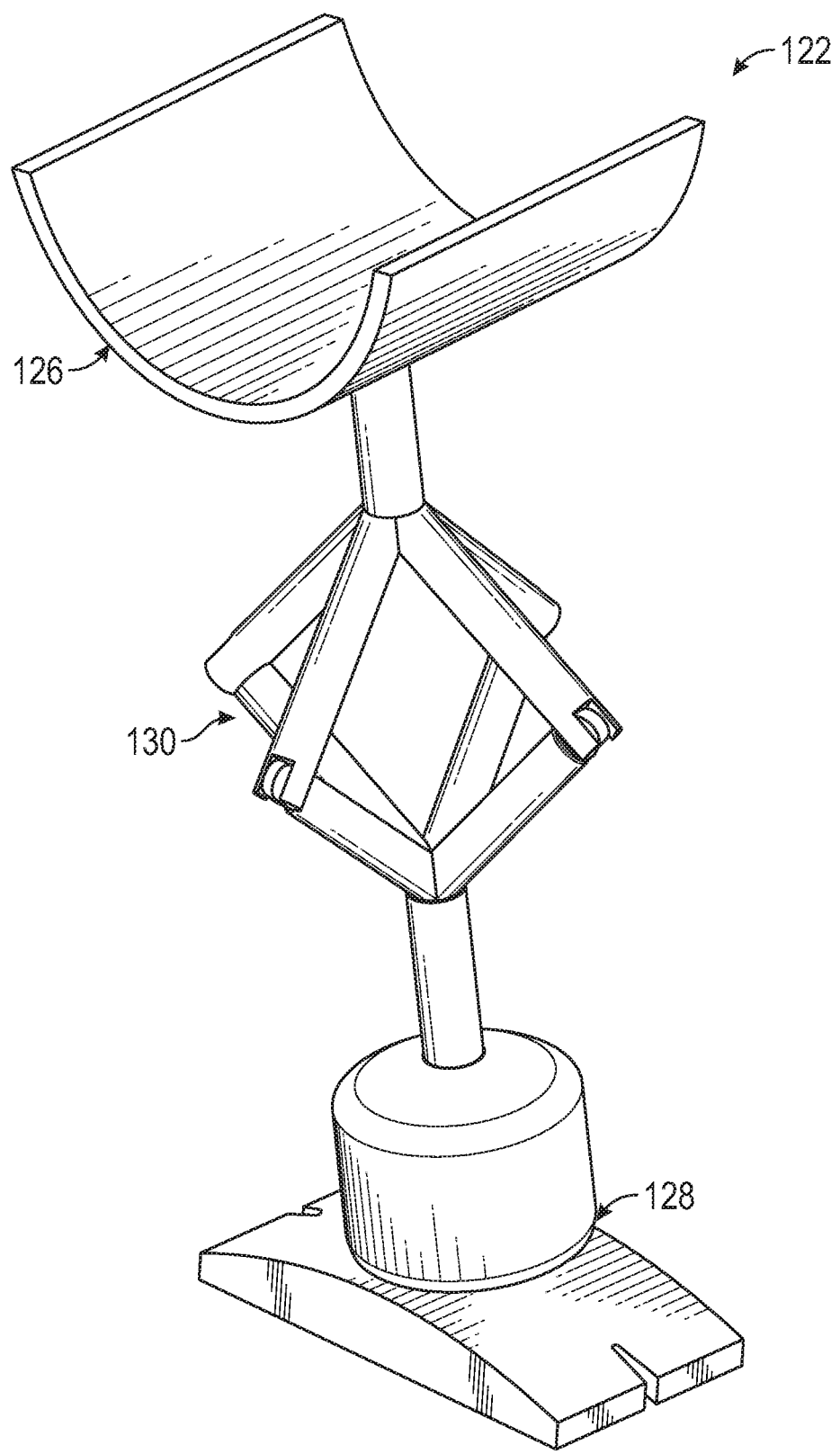
FIG. 7 illustrates another exemplary design configuration of the prosthetic device of FIG. 6.

The first fastening segment 126 and the second fastening segment 128 of the prosthetic device 122 may include various other designs depending on the clinical need. For example, in the non-limiting embodiment of FIG. 7, the first fastening segment 126 includes a U-shaped cradle that rests on the undersurface of the malleus and the second fastenings segment 128 includes a shoe that contacts the footplate of the stapes. The design of FIG. 7 is particularly suited for a total incus-stapes reconstruction.

Figure 8:
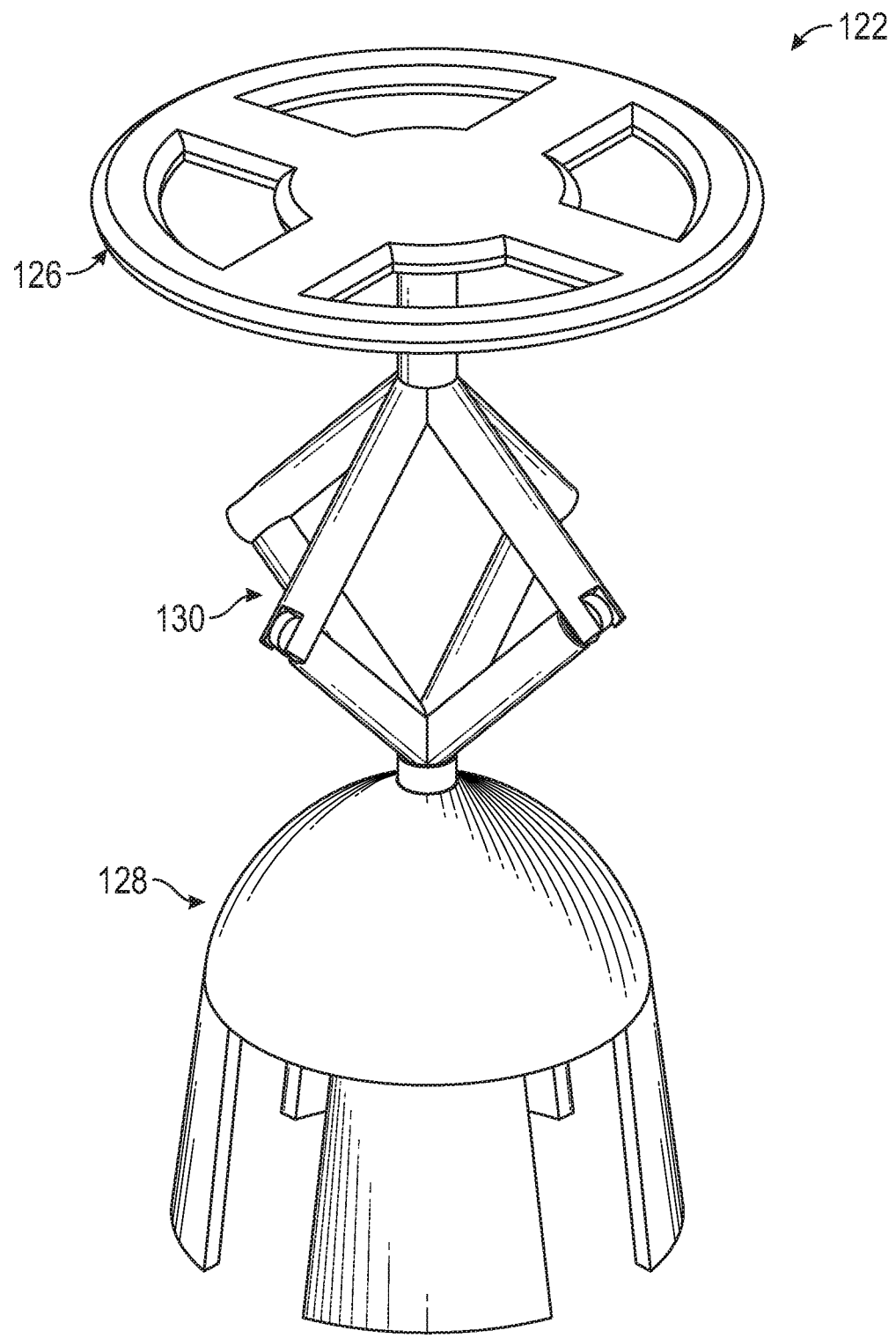
FIG. 8 illustrates another exemplary design configuration of the prosthetic device of FIG. 6.

The prosthetic device 122 may also be configured to achieve partial ossicular chain reconstructions. For example, as shown in the non-limiting embodiment of FIG. 8, the first fastening segment 126 includes a flat disk that contacts the tympanic membrane and the second fastening segment 128 includes a cupped socket that can be received on the capitulum of the stapes. The design of FIG. 8 is particularly suited for a partial ossicular reconstruction that reconstructs the incus.

Figure 9:
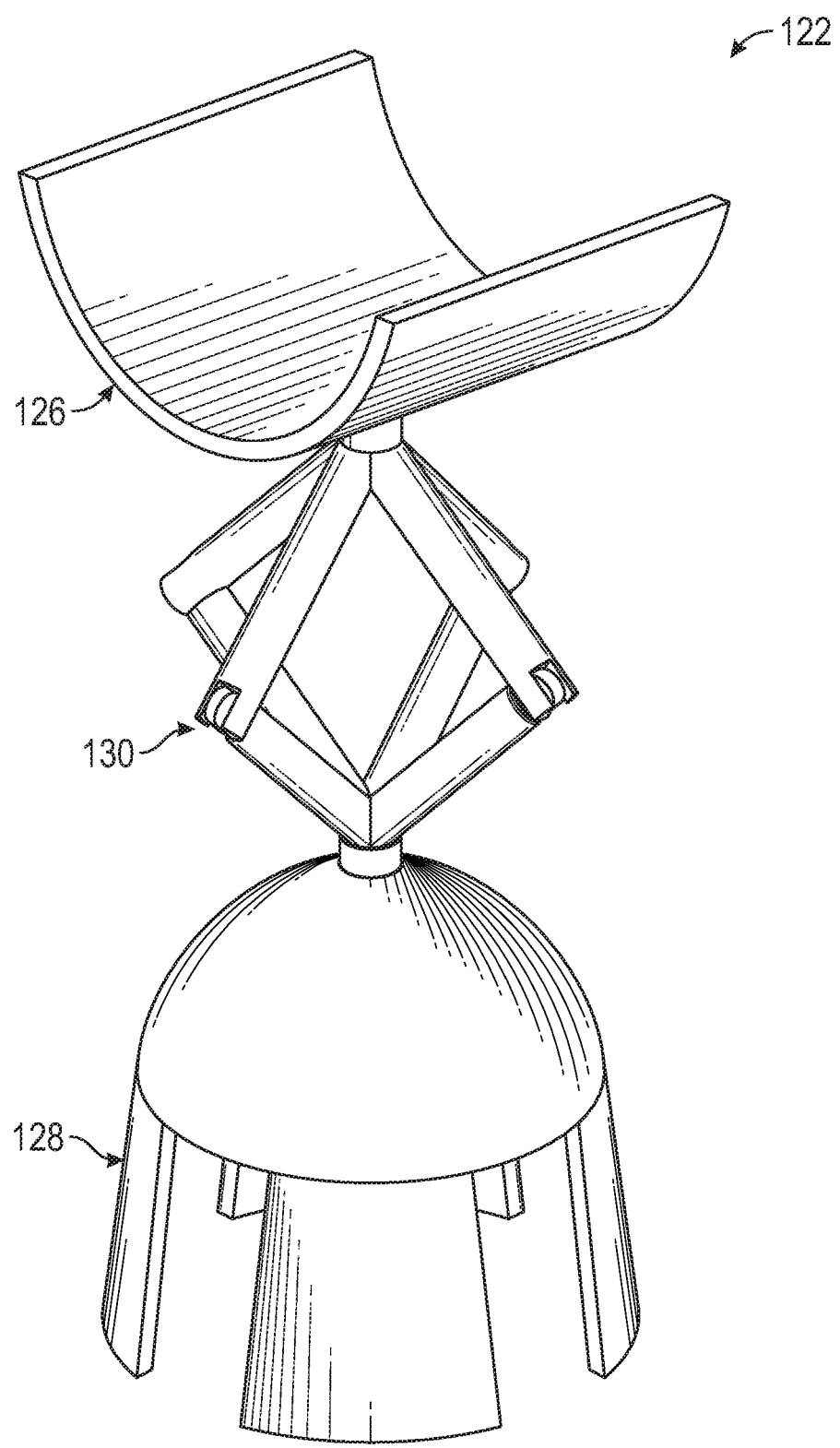
FIG. 9 illustrates yet another exemplary design configuration of the prosthetic device of FIG. 6.

In yet another non-limiting embodiment, shown in FIG. 9, the first fastening segment 126 includes a U-shaped cradle that rests on the undersurface of the malleus and the second fastenings segment 128 includes a cupped socket that can be received on the capitulum of the stapes. The design of FIG. 9 is particularly suited for a partial ossicular reconstruction that reconstructs the incus.

Figure 10:
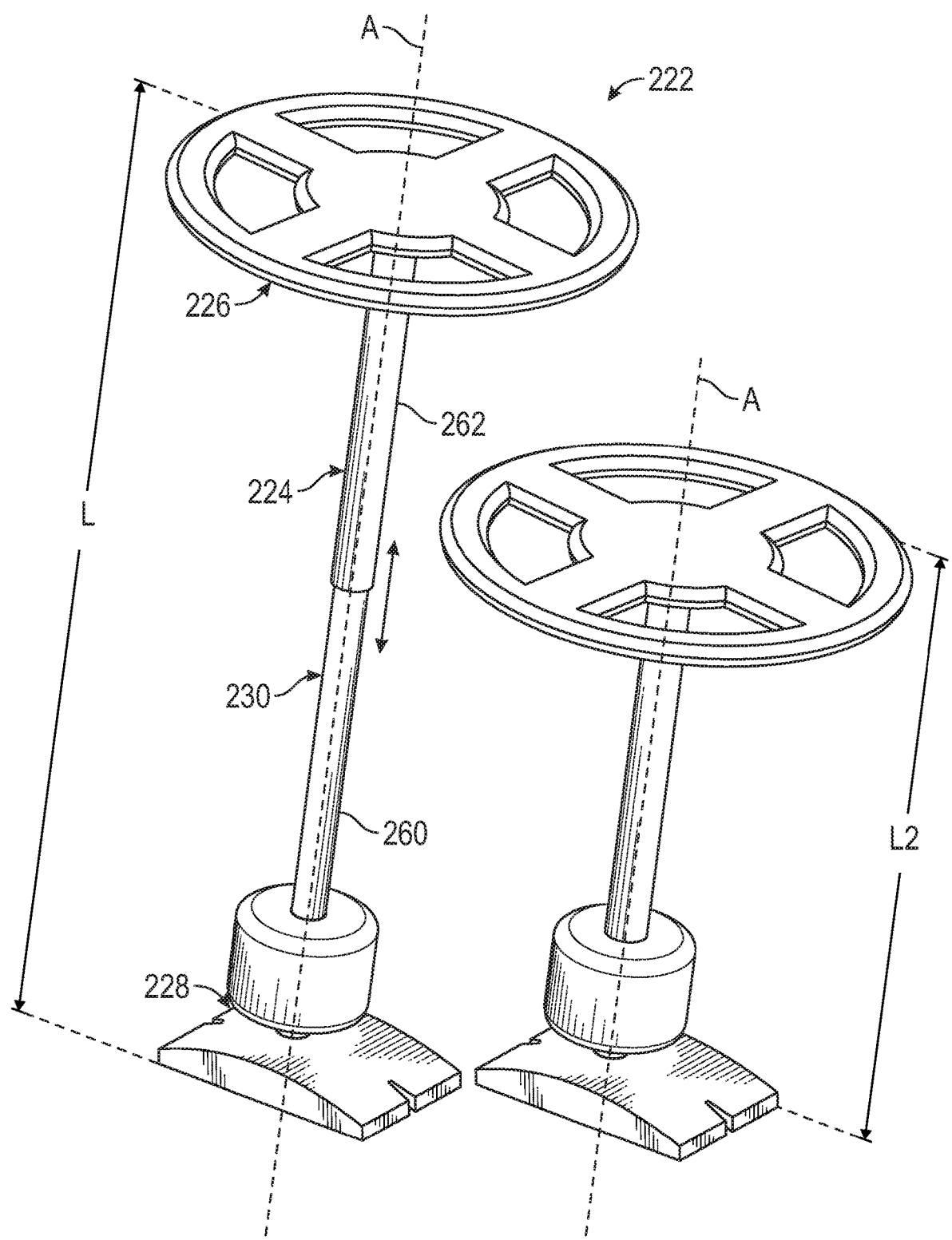
FIG. 10 illustrates a prosthetic device according to a third embodiment of this disclosure.

FIG. 10 illustrates yet another exemplary prosthetic device 222 for performing ossicular reconstructions. The prosthetic device 222 includes a body 224 disposed along a longitudinal axis A. The body 224 includes a first fastening segment 226, a second fastening segment 228, and a central segment 230 connected between the first fastening segment 226 and the second fastening segment 228. The first fastening segment 226 is configured for connecting the prosthetic device 222 to the tympanic membrane or a component of the ossicular chain, and the second fastening segment 228 is configured for connecting the prosthetic device 222 to another component of the ossicular chain, or to contact tissues adjacent to the inner ear.

The central segment 230 is adjustable to alter a length L of the body 224 along the longitudinal axis A. The length L may be decreased or increased by adjusting the central segment 230 in a direction that is coaxial to the longitudinal axis A.

In a non-limiting embodiment, the central segment 130 includes a telescoping assembly design having a rod 260 and a tube 262. The rod 260 is movable within the tube 262 along the longitudinal axis A to adjust the length L of the prosthetic device 222. For example, in a non-limiting embodiment, the length L can be decreased to a length L2 by moving the rod 260 a greater distance into the tube 262 (see right hand picture of FIG. 10). In another non-limiting embodiment, the length L can be increased by pulling the rod 260 a greater distance out of the tube 262 (see left hand picture of FIG. 10). The adjustment of the length L can be made either in situ or ex situ after determining the desired length of the prosthetic device 222. The length L can be fixed by crimping the tube 262 to the rod 260, such as by using surgical pliers, a hemostat, or some other common surgical instrument.

The central segment 230 can also be modified to adjust an angulation of the prosthetic device 222. For example, in another non-limiting embodiment, the central segment 230 can be bent such that it extends at an off-axis angle relative to the longitudinal axis A. In the off-axis position, the body 224 of the prosthetic device 222 is non-linear along the longitudinal axis A.

The prosthetic device 222 of FIG. 10 is particularly suited for a total ossicular reconstruction that substantially reconstructs each of the malleus, the incus, and the stapes. In this non-limiting embodiment, the first fastening segment 226 includes a flat disk that contacts the tympanic membrane and the second fastening segment 228 includes a shoe that contacts the footplate of the stapes. In another non-limiting embodiment, the second fastening segment 228 includes a ball joint 244 that allows the shoe to swivel relative to the rest of the prosthetic device 222.

Figure 11:
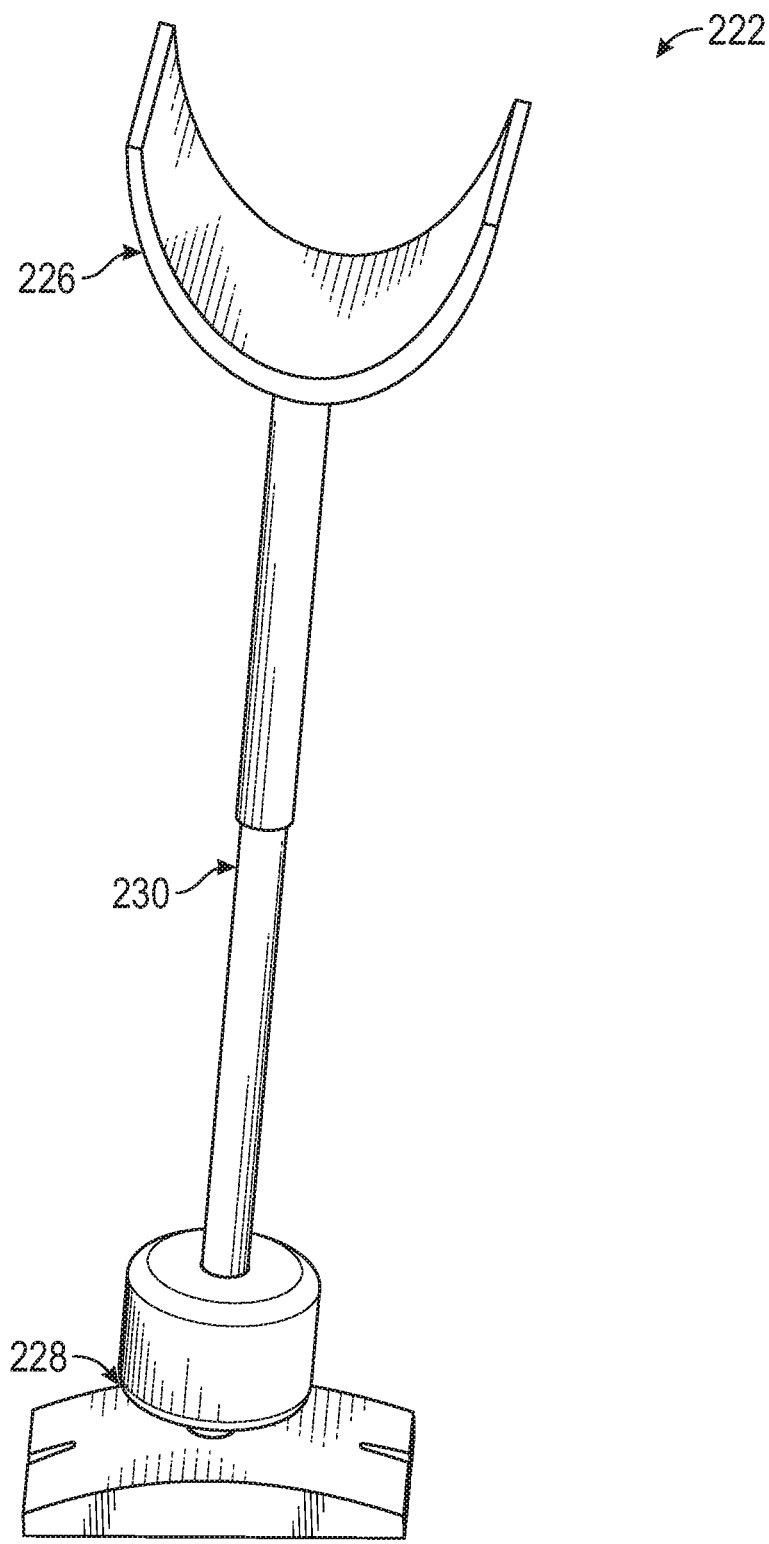
FIG. 11 illustrates another exemplary design configuration of the prosthetic device of FIG. 10.

The first fastening segment 226 and the second fastening segment 228 of the prosthetic device 222 may include various other designs depending on the clinical need. For example, in the non-limiting embodiment of FIG. 11, the first fastening segment 226 includes a U-shaped cradle that rests on the undersurface of the malleus and the second fastenings segment 228 includes a shoe that contacts the footplate of the stapes. The design of FIG. 11 is particularly suited for a total incus-stapes reconstruction.

Figure 12:
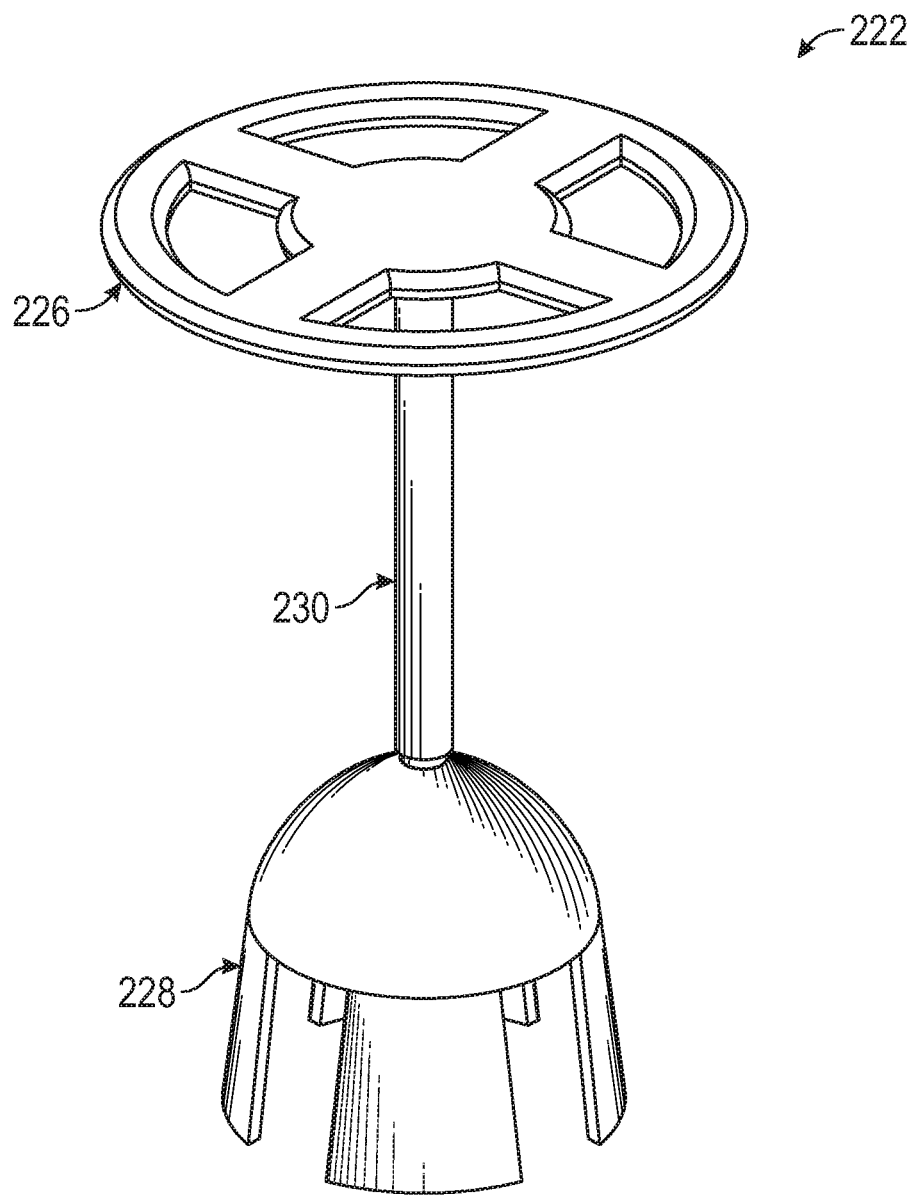
FIG. 12 illustrates another exemplary design configuration of the prosthetic device of FIG. 10.

The prosthetic device 222 may also be configured to achieve partial ossicular chain reconstructions. For example, as shown in the non-limiting embodiment of FIG. 12, the first fastening segment 226 includes a flat disk that contacts the tympanic membrane and the second fastening segment 228 includes a cupped socket that can be received on the capitulum of the stapes. The design of FIG. 12 is particularly suited for a partial ossicular reconstruction that reconstructs the incus.

Figure 13:
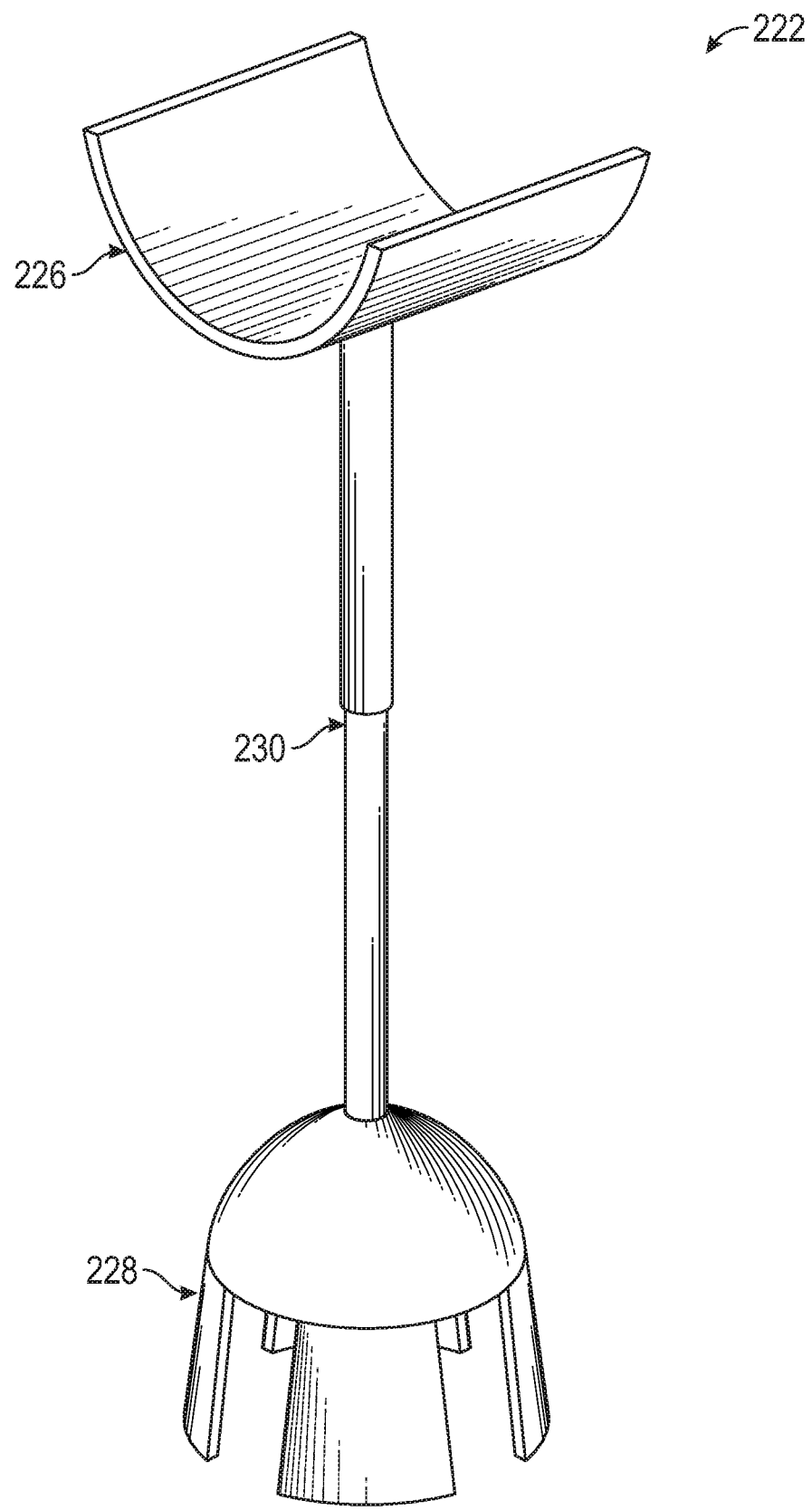
FIG. 13 illustrates yet another exemplary design configuration of the prosthetic device of FIG. 10.

In yet another non-limiting embodiment, shown in FIG. 13, the first fastening segment 226 includes a U-shaped cradle that rests on the undersurface of the malleus and the second fastening segment 228 includes a cupped socket that can be received on the capitulum of the stapes. The design of FIG. 13 is particularly suited for a partial ossicular reconstruction that reconstructs the incus.

Figure 14:
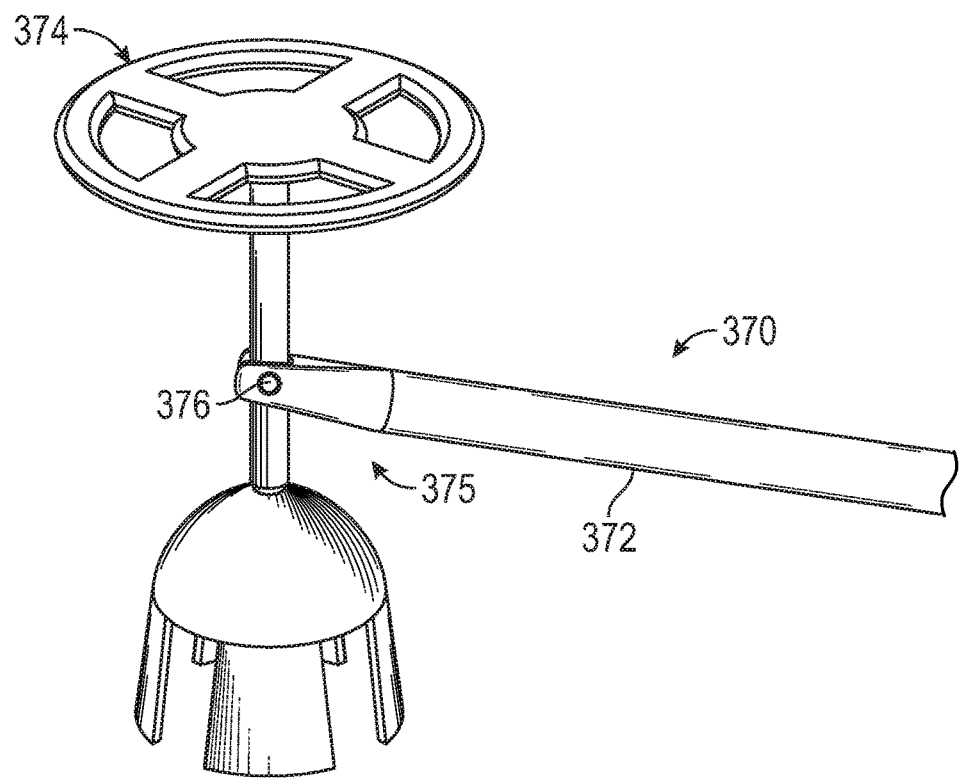
FIG. 14 illustrates a micro-measuring device according to a first embodiment of this disclosure.

FIG. 14 illustrates an exemplary micro-measuring device 370 for performing ossicular reconstructions. The micro-measuring device 370 may be used to accurately assess the distances and angles between middle ear structures during an ossicular reconstruction procedure. These distances and angles may then be used accurately select and size a prosthetic device having a desired length and angulation. The micro-measuring device 370 could be either a disposable device or a reusable device.

The micro-measuring device 370 may include an elongated shaft 372 and a template 374 pivotally connected to the elongated shaft 372. In a non-limiting embodiment, the template 374 is connected to the elongated shaft 372 by a pin 376. Other types of connections are also contemplated within the scope of this disclosure. The template 374 may be connected at a distal end 375 of the elongated shaft 372.

The template 374 may include any size and shape and generally mimics a size and shape of a prosthetic device for an ossicular reconstruction. The micro-measuring device 370 could be provided as part of a set of measuring devices with each measuring device having a template of a different shape and/or size from the other measuring devices.

In another non-limiting embodiment, the template 374 of the micro-measuring device 370 includes an adjustable shape similar to that of any of the adjustable prosthetic devices disclosed herein (see, e.g., FIGS. 2-13). In such an embodiment, only a single measuring device is required for any given clinical need.

The micro-measuring device 370 is inserted into the middle ear and is then positioned as desired relative to the ossicular chain. The template 374 may be pivoted, swiveled, or otherwise maneuvered relative to the elongated shaft 372 to achieve a desired positioning. In particular, the micro-measuring device 370 may be maneuvered to assess the length and angulation necessary for reconstructing the ossicular chain, or portions thereof. Once the length and angulation has been accurately accessed using the micro-measuring device 370, a prosthetic device similar to those discussed above can be adjusted by the surgeon to embody the length and angulation that matches the clinical need.

Figure 15:
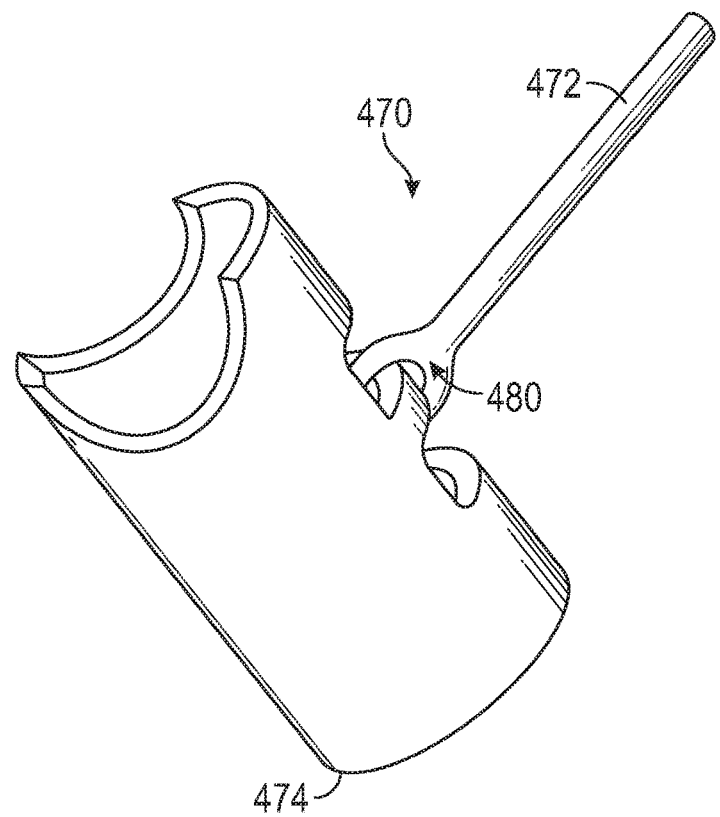
FIG. 15 illustrates a micro-measuring device according to a second embodiment of this disclosure.

FIG. 15 illustrates another exemplary micro-measuring device 470 for performing ossicular reconstructions. The micro-measuring device 470 may be a disposable or a reusable device.

The micro-measuring device 470 may include an elongated shaft 472 having a cupped end 480. The cupped end 480 may receive a portion of a template 474 for pivotally connecting the template 474 to the elongated shaft 472. The template 474 may include any size and shape and could include an adjustable shape similar to any of the adjustable prosthetic devices disclosed herein (see, e.g., FIGS. 2-13) such that only a single measuring device is required for any given clinical need.

The micro-measuring device 470 is inserted into the middle ear and is then positioned as desired relative to the ossicular chain. The template 474 may be pivoted, swiveled, or otherwise maneuvered relative to the elongated shaft 472 to achieve a desired positioning. The micro-measuring device 470 may be used to provide an accurate assessment of the length and angulation necessary for reconstructing the ossicular chain or portions thereof. Once the length and angulation has been accessed using the micro-measuring device 470, a prosthetic device similar to those discussed above can be adjusted by the surgeon to embody the length and angulation that matches the clinical need.

Figure 16:
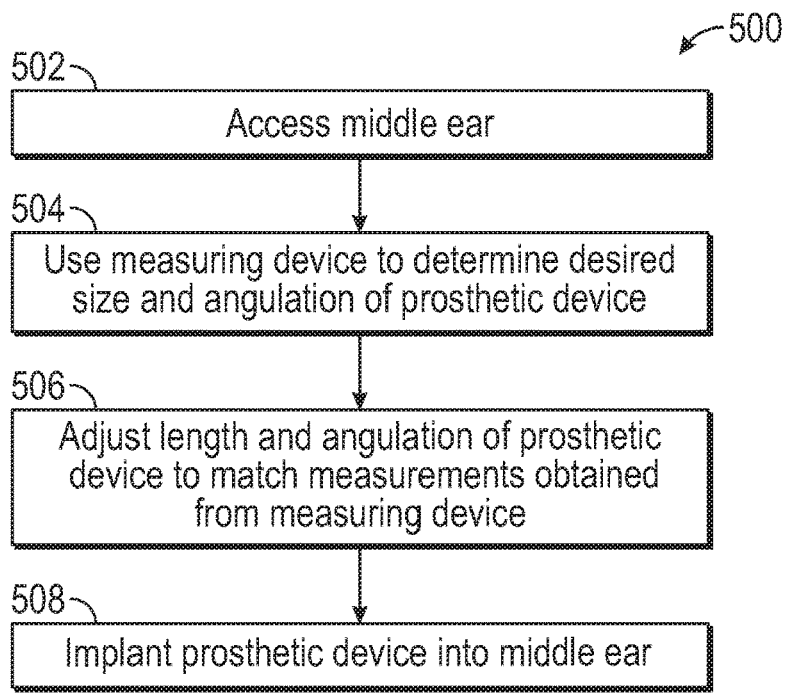
FIG. 16 schematically illustrates a method of performing an ossicular reconstruction.

FIG. 16, with continued reference to FIGS. 1-15, schematically illustrates an exemplary method 500 for performing an ossicular reconstruction. The method begins at block 502 by creating access to the middle ear 10. An incision may be made, and then the skin surrounding the incision may be flipped up to access the middle ear 10. The ossicular chain can then be examined to determine the extent of any disease/damage.

Next, a block 504, the micro-measuring device 370, 470 is used to determine a desired size and angulation of a prosthetic device 22, 122, 222. Other known measuring techniques could alternatively be utilized.

The length and angulation of the prosthetic device 22, 122, 222 is adjusted at block 506 based on the measurements obtained at block 504. This can be done either in situ or ex situ.

Figure 17:
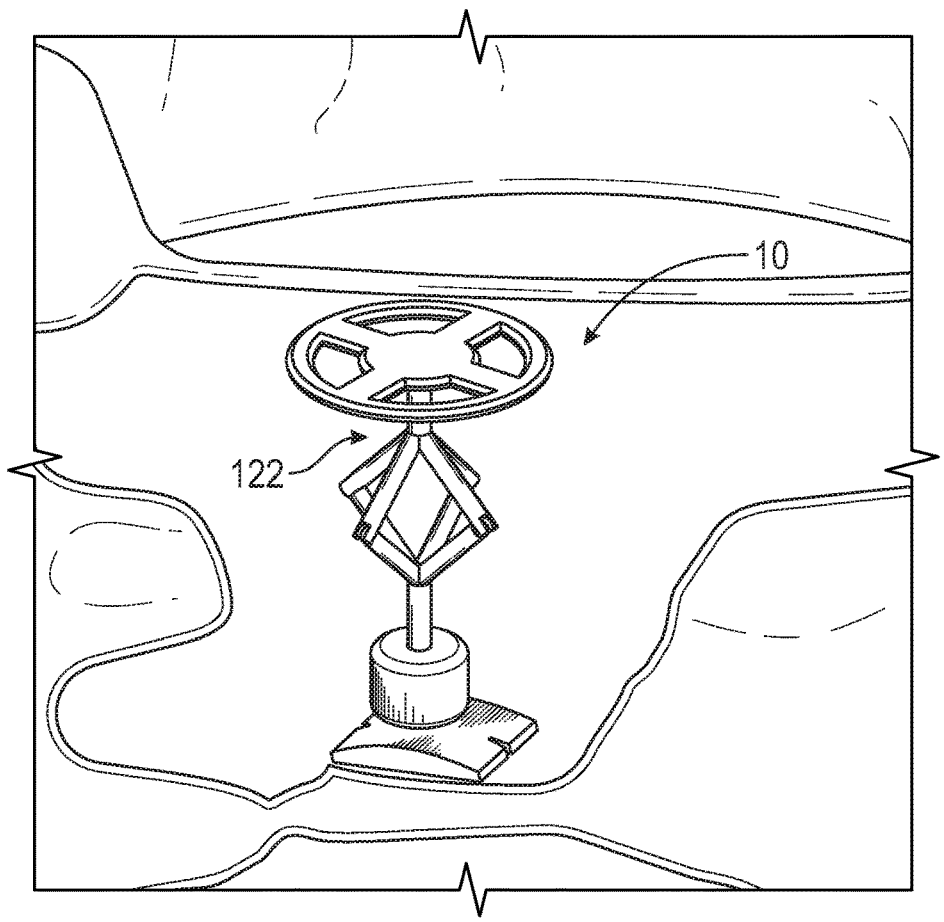
FIG. 17 illustrates a prosthetic device implanted in a human middle ear to reconstruct portions of an ossicular chain.

Finally, at block 508, the appropriately sized and angulated prosthetic device 22, 122, 222 is implanted into the middle ear 10 to reconstruct the ossicular chain or portions thereof. FIG. 17 shows one example of the prosthetic device 122 of FIG. 6 implanted into the middle ear 10 to reconstruct the ossicular chain.

Once the prosthetic device 22, 122, 222 has been properly positioned, it may be stabilized using commonly employed microsurgical techniques including the use of gel foam and/or other materials to stabilize the prosthetic device 22, 122, 222 and any reconstructive material for tympanoplasty such as fascia or cartilage. The tympanic membrane is replaced and the ear canal packed with similar materials to stabilize the lateral aspect of the tympanic membrane.

The adjustable prosthetic devices and micro-measuring devices of this disclosure reduce surgical time, reduce surgical costs typically associated with discarding unsuitably sized prostheses, and obviate the complication of misplaced templates in the recesses of the middle ear.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A prosthetic device for performing ossicular reconstructions, comprising:
   a body extending along a longitudinal axis, the body including a first fastener segment, a second fastener segment, and a central segment between the first fastening segment and the second fastening segment; and
   the central segment is adjustable to either lengthen or shorten the body in a direction that is coaxial with the longitudinal axis,
   wherein the central segment includes a plurality of arched plates that are arranged together to form a spherical shape.

2. The prosthetic device as recited in claim 1, wherein a portion of the central segment includes an adjustable angle to position the body non-linearly along the longitudinal axis.

3. The prosthetic device as recited in claim 1, wherein the first fastener segment is configured for connecting the body to a tympanic membrane or a component of an ossicular chain, and the second fastener segment is configured for connecting the body to tissue near an inner ear or another component of the ossicular chain.

4. The prosthetic device as recited in claim 3, wherein the first fastener segment is either a flat disk or a U-shaped cradle.

5. The prosthetic device as recited in claim 4, wherein the second fastener segment is either a shoe or a cupped socket.

6. The prosthetic device as recited in claim 1, wherein each of the plurality of arched plates are compressible to shorten the body and straightenable to lengthen the body.

7. The prosthetic device as recited in claim 1, wherein each of the plurality of arched plates includes at least one fenestration formed through a body of each of the plurality of arched plates.

8. The prosthetic device as recited in claim 1, comprising a first shaft extending from a first part of the central segment to the first fastener segment and a second shaft extending from a second part of the central segment to the second fastener segment.

9. The prosthetic device as recited in claim 1, wherein the plurality of arched plates includes at least four arched plates arranged to form the spherical shape.

10. A method for performing an ossicular reconstruction, comprising:
    inserting a measuring device into a middle ear,
    wherein the measuring device includes an elongated shaft and a template movably connected to the elongated shaft;
    determining, via the measuring device, a size and an angulation of a prosthetic device that is necessary for reconstructing at least a portion of an ossicular chain of the middle ear;
    adjusting a length and an angulation of the prosthetic device to match the measurements obtained from the measuring device; and
    implanting the prosthetic device into the middle ear.

11. The method as recited in claim 10, wherein adjusting the length and the angulation of the prosthetic device occurs before implanting the prosthetic device into the middle ear.

12. The method as recited in claim 10, wherein adjusting the length and the angulation of the prosthetic device occurs after implanting the prosthetic device into the middle ear.

13. The method as recited in claim 10, comprising readjusting the length or the angulation of the prosthetic device after implanting the prosthetic device into the middle ear.

14. The method as recited in claim 10, wherein determining the size and the angulation of the prosthetic device includes:
    maneuvering the template of the measuring device to achieve a desired positioning of the template relative to the ossicular chain; and
    assessing the length and the angulation necessary for reconstructing the ossicular chain based on the positioning of the template.

15. The method as recited in claim 10, wherein adjusting the length and the angulation of the prosthetic device includes manipulating an arched plate of the prosthetic device.

16. The method as recited in claim 10, wherein adjusting the length and the angulation of the prosthetic device includes manipulating a jointed limb of the prosthetic device.

17. The method as recited in claim 10, wherein adjusting the length and the angulation of the prosthetic device includes manipulating a telescoping tube assembly of the prosthetic device.

18. A system for performing ossicular reconstructions, comprising:
    an adjustable prosthetic device; and
    a measuring device including an elongated shaft and a template movably connected to the elongated shaft,
    wherein the template includes a size and a shape corresponding to that of the adjustable prosthetic device for reconstructing at least a portion of an ossicular chain of an inner ear.

19. The system as recited in claim 18, wherein the adjustable prosthetic device extends along a longitudinal axis and includes a first fastener segment, a second fastener segment, and a central segment between the first fastening segment and the second fastening segment, wherein the central segment includes a plurality of arched plates that are arranged together to form an adjustable spherical shape.

20. The system as recited in claim 18, wherein the elongated shaft includes a cupped end adapted to receive a portion of the template for pivotally connecting the template to the elongated shaft.

21. The system as recited in claim 18, wherein the template is pivotally connected to a distal end of the elongated shaft by a pin.

22. The system as recited in claim 18, comprising a second measuring device that includes a second elongated shaft and a second template movably connected to the second elongated shaft, and wherein the second template includes a different size and a different shape than the template of the measuring device.

* * * * *